United States Patent [19]

Manning

[11] Patent Number: 4,463,211

[45] Date of Patent: Jul. 31, 1984

[54] PROCESS FOR OLIGOMERIZATION OF $C_2$ TO $C_{10}$ NORMAL OLEFINS

[75] Inventor: Harold E. Manning, Houston, Tex.

[73] Assignee: Petro-Tex Chemical Corporation, Houston, Tex.

[21] Appl. No.: 425,106

[22] Filed: Sep. 27, 1982

Related U.S. Application Data

[63] Continuation of Ser. No. 199,840, Oct. 23, 1980, abandoned.

[51] Int. Cl.³ ............................................. C07C 2/04
[52] U.S. Cl. .................................. 585/510; 585/515; 585/520; 585/526
[58] Field of Search ................ 585/515, 526, 510, 520

[56] References Cited

FOREIGN PATENT DOCUMENTS 973555 10/1964 United Kingdom ........... 585/515 X

Primary Examiner—Paul F. Shaver
Attorney, Agent, or Firm—Kenneth H. Johnson

[57] ABSTRACT

A process for the oligomerization of normal $C_2$–$C_{10}$ olefins, for example n-butenes by passing a feed containing said olefins in liquid phase through a fixed bed of acid, cation exchange resin at a temperature in the range of 40° to 185° C. at LHSV of 0.10 to 10 and recovering the oligomer product. In the case of n-butenes the principal component of the oligomer product is $C_8$ dimer.

7 Claims, 3 Drawing Figures

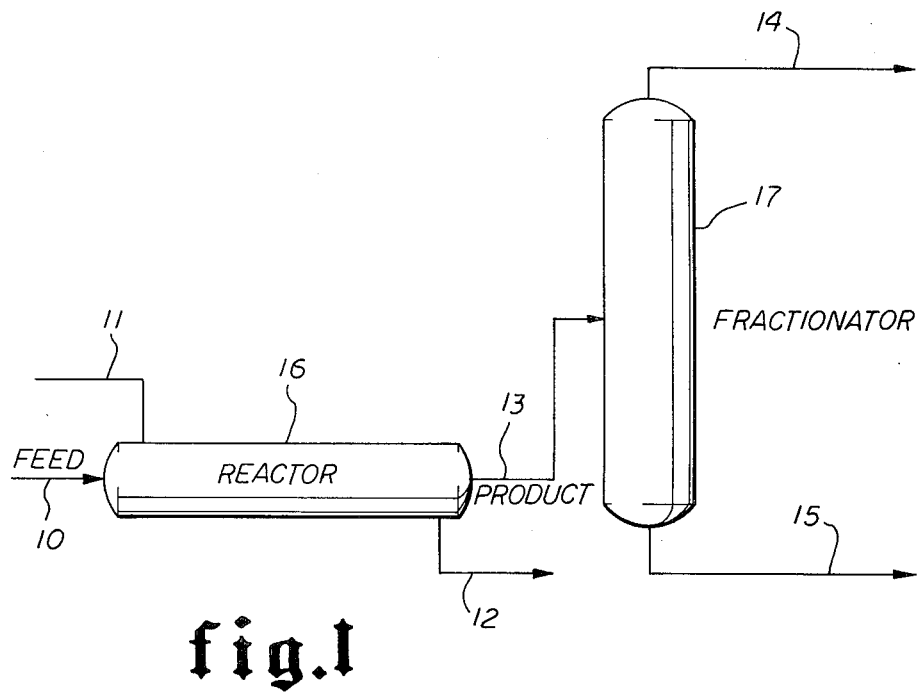
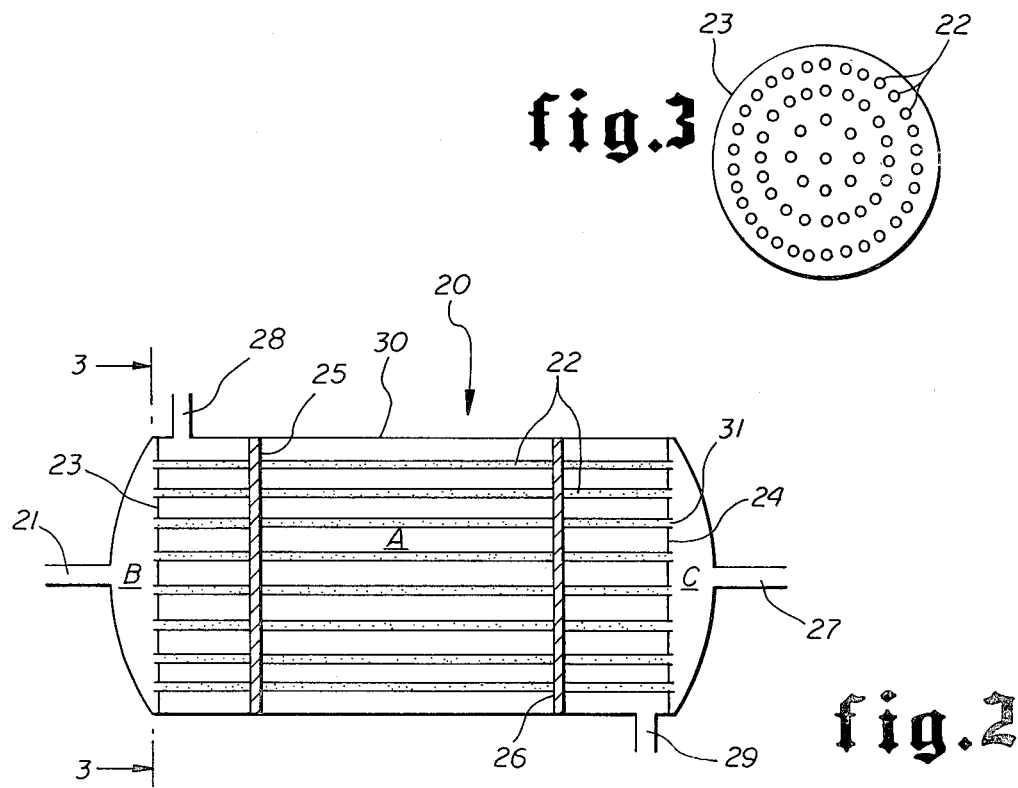

PROCESS FOR OLIGOMERIZATION OF $C_2$ TO $C_{10}$ NORMAL OLEFINS

This is a continuation of application Ser. No. 199,840, filed Oct. 23, 1980, now abandoned.

BACKGROUND OF THE INVENTION

1. Field of the Invention

The present invention relates to a novel process for the production of oligomers of normal olefins of $C_2$ to $C_{10}$ carbon atoms and in particular $C_8$ olefins by the dimerization of n-butenes.

2. Prior Art

The reaction of olefins to form longer chains of two or more monomer units is well known. It is well known that ethylene and other olefins can be polymerized to form relatively low molecular weight products through the use of certain organo-metallic catalyst. Broadly, these catalysts are compounds of metals of groups IV to VI of the Periodic Table of elements in combination with other compounds of metals of groups I to III. The Ziegler catalysts are representatives of such catalysts and are preferably specific combinations of titanium halide and a trialkyl aluminum component, with or without other metal promoters. Other catalysts such as alkyl aluminum halides (preferably the chloride) in combination with alkyl titanium esters have also been used to carry out this reaction.

These catalysts are homogeneous in that they are soluble in the reaction medium. The catalysts are very effective, that is the reaction can easily be carried out to produce high molecular weight compounds, with the appropriate amounts of catalyst. In some instances, by using extremely low concentrations of catalyst in the reaction system, low molecular weight products may be produced, in particular dimers, trimers and tetramers.

Free radicals, carbonium ions and carbanions have also been used to promote the reaction of olefins, particularly alpha-olefins to produce polymers of high molecular weight.

The use of acid catalysts such as sulfuric acid to selectively react isoolefins in the presence of other olefins to produce lower molecular weight products, e.g., U.S. Pat. Nos. 3,564,317 and 3,832,418 is also well known. U.S. Pat. No. 4,065,512 discloses the use of perfluorosulfonic acid resin, particularly in the form of films for the polymerization of isobutene to produce dimers, trimers and higher oligomers.

More recently, U.S. Pat. No. 4,215,011 disclosed the use of acid cation exchange resin in a heterogenous combination reaction-distillation system for the selective dimerization of isobutene in the presence of normal butenes. The reaction is highly preferential for the reaction of isobutene with itself, although some codimer between n-butenes and isobutene are formed, and provides a means to separate isobutene from a $C_4$ stream.

It would appear from the art that normal butenes are not reactive, other than with isobutene in the presence of acid catalyst or acid cation exchange resin.

SUMMARY OF THE INVENTION

The present process, briefly, is a process for the production of oligomers, i.e., principally dimers, trimers and tetramers of normal $C_2$ to $C_{10}$ olefins, preferably $C_3$ to $C_5$ normal olefins in liquid phase in the presence of acid cation exchange resins at temperatures in the range of 40° to 185° C., preferably above 70° C. and more preferably above 80° C.

In particular, it has now been found that normal butenes, both butene-1 and butene-2 are reactive to form oligomers, in particular dimers, in liquid phase in the presence of acid cation exchange resins at temperatures in the recited range of 40° to 185° C. (preferably from 70° C.). Preferably the temperature is in the range of 80° to 130° C. The temperature of the reaction is determined by standard means using type K thermocouple probe. Generally a longer residence time of the reactants in the catalyst bed is used at the lower reaction temperatures. Thus, over the range of temperatures disclosed, residence times expressed as, liquid hourly space velocity (LHSV) of 0.10 to 10 preferably 2 to 5 LHSV, would be employed and adjusted to obtain the maximum yield of oligomers. Lower reaction temperatures in the recited range would be used with longer residence times of the reactants in the catalyst bed.

BRIEF DESCRIPTION OF THE DRAWING

FIG. 1 is a schematic depiction of a preferred embodiment of the present process.

FIG. 2 is a cross sectional elevation of a reactor for carrying out the process of the present invention.

FIG. 3 is a cross sectional view of the reactor of FIG. 2 taken along line 3—3.

DETAILED DESCRIPTION OF THE INVENTION

In the case of normal butenes, a very interesting result of the present process is that the reaction product is a similar mixture notwithstanding whether the monomer feed is butene-1 or butene-2 or a mixture of the two. It should be appreciated that any isobutene present in the reaction system is preferably reacted, either to form dimer or codimer with the normal butenes. Thus, the amount of isobutene present should be minimized so as not to alter or change the purity of the desired normal butene dimerization product. The feed to the reactor should contain no more than 10 mole percent isoolefin and preferably less than 5 mole percent thereof. Most preferably the feed will contain less than 1 mole percent of the isoolefin. Larger amounts of isobutene result in a product of sufficiently different characteristics from the n-butene dimer product that the product may not be useful for the purposes for which the n-butene dimer is employed.

The product of the normal butenes oligomerization reaction contains in addition to n-butene dimer, codimer of isobutene or diisobutene, if isobutene is present in the reaction system, and higher oligomers of the normal butenes and/or isobutene, usually trimers and tetramers. In the reactor the normal $C_4$ olefins contact the catalyst and react to form a polymer predominately of number average molecular weight of a $C_{16}$ hydrocarbon or less. Some higher polymers of non-specific configuration may be formed as very minor by-products. The various components of the product stream, e.g., n-butene dimer, trimer, etc., are separated by distillation.

The dimer portion of the reaction product of normal butenes according to the present invention is surprisingly linear compared to similar materials made by prior procedures. The n-butene dimer product of the present invention is principally dimethyl hexenes, with some methyl heptenes and with very little of the trimethyl pentenes, i.e., less than 5 mole % (typically less than 1–3 mole % with the dimer product being 3,4-dimethylhexenes. This product composition differs significantly to that obtained for example from phosphoric acid oligomerizations of normal butenes which typically produce considerably more of the trimethyl pentenes (10 to 80 times more).

The feed in the present process may contain olefins of various carbon chain lengths, and the products will be a mixture of the reaction of the various olefins, particularly n-olefins present, e.g., a n-butene, propylene feed will produce $C_8$, $C_7$ and $C_6$ dimer products as well as the higher oligomers of the various monomers present. The feed to the reactor should be free of any entrained, second phase water.

In the case of normal-butene the location of the double bond, i.e., in the 1 or 2 position, has not proved to be of critical significance in carrying out the reaction. However, in normal olefins of longer chains, e.g., 5 to 10 carbon atoms, the location of the double bond in the alpha position would facilitate the reaction.

Although the present process can be carried out batchwise, it is contemplated that in actual practice the process will be operated continuously with a separation of unreacted normal olefins and recycle of a portion thereof to the reactor.

The product of the reaction is a low molecular weight polymer, i.e., oligomer which is a predominately dimers, but containing some trimers and tetramers of the olefins in the feed. The term "predominate amount" or "predominately" as used herein means over 60 mole %. The unreacted materials in the product stream are not considered to be product. Hence, if the conversion of normal olefins is 33% of those present, the product stream will contain 67% unreacted material and 33% of the reacted material which will preferably comprise at least 80 mole % of the dimer, trimer and tetramer.

The nature of the catalyst is such that in carrying out the polymerization of the normal olefins as described, there is no tendency to produce any substantial amounts of higher polymers, that is, the principal or predominate reaction products are tetramers or lower polymers, i.e., trimers and dimers, with a strong tendency to favor the dimers.

Generally the reaction as described is carried out with streams containing at least 10 mole % of the normal olefin to be oligomerized, preferably 50 mole % up to substantially pure feeds of the normal olefins, and more preferably the feed to the reactor and catalyst bed contains at least 70 mole % of the normal olefins. At very low concentrations of normal butenes the isoolefin should likewise be low. Preferably the normal olefins will comprise at least 60 mole % and more preferably 90 mole % or more of the olefins present, particularly in view of the greater reactivity of the corresponding isoolefins.

It is, of course, apparent that the ethylene and propylene have only the one form, corresponding to normal olefins of $C_4$ to $C_{10}$, however, for simplicity all of the olefins within the scope of the present invention are designated as "normal".

In addition to the normal olefins, normal paraffins may be present and have not been of any significance in carrying out the present process. In addition to the linear paraffins, branched paraffins may be present.

Catalysts suitable for the new process are cation exchangers, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A variety of methods may be used for preparing these polymers; for example, polymerization alone or in admixture with other monovinyl compounds, or by crosslinking with polyvinyl compounds; for example, with divinyl benzenes, divinyl toluenes, divinylphenylethers and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfonic acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contains sulfur trioxide. The treatment with fuming sulfuric acid is preferably carried out at 0° to 150° C., and the sulfuric acid should contain unreacted sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent Specification No. 908,247).

The ion exchange resin is preferably used in a granular size of about 0.25 to 2 mm, although particles from 0.15 mm up to about 2 mm may be employed. The finer catalysts provide high surface area, but also result in high pressure drops through the reactor. Both gel types and the macroreticular form of these catalysts may be employed. In a preferred embodiment, the catalyst is the macroreticular form which has surface areas of from about 20 to 600 square meters per gram preferably about 20–50 square meters per gram. The catalyst is employed in a fixed bed.

The reaction is carried on in liquid phase and sufficient pressure is employed in the system to maintain the liquid phase under the conditions of reaction. For the full range of $C_2$ to $C_{10}$ normal olefins, the pressure would range from about 50 psig to 3500 psig; however for $C_3$ to $C_5$ normal olefins, pressures would be in the range of 75 to 800 psig.

In carrying out the present process, it was determined that temperature of the catalyst (which reflects the exotherm in the catalyst bed) was of particular importance. The temperature range of 40° to 185° C. reflects the operable range which may be used to carry out the reaction over a useful time trend of the catalyst, which tends to decline in activity at higher temperatures. The nature of the catalyst too, requires the control of the upper temperature, since it can be deactivated by excessive temperatures in the bed. The maximum temperature which the catalyst can withstand varies with its particular characteristics, and even for the high temperature types (stated to be in the range of 175°–200° C. for aqueous systems), in the present process a rapid decline in activity is noted above 190° C. Further, temperatures above 150° C. tend to promote trimer formation.

The feed to the catalyst should be free or substantially free of catalyst poisons such as organic or inorganic bases or metal cations. The feed may contain controlled amounts of water or alcohol, not sufficient to form a second phase in the feed, to serve as catalyst modifiers to maintain the catalyst performance.

The term liquid hourly space velocity (LHSV) means the liquid volumes of hydrocarbon per volume of reactor containing catalyst, per hour.

Referring to FIG. 1, a schematic representation of a preferred embodiment of the present process is shown. A normal olefin containing feed stream enters reactor 16 via line 10 where it is contacted with the resin catalyst (not shown). The reaction temperature is maintained constant by means of a fluid medium entering the reactor through line 11 where it is in indirect contact with the catalyst to either remove heat or supply heat, such as on start-up. The fluid medium exits the reactor via line 12 and is treated elsewhere as required to maintain the desired temperature in the reactor.

The fluid medium can be any fluid capable of providing indirect heat exchange with the fixed bed catalyst. Water, air, steam or organic liquids could be employed for this purpose.

In the reactor, the olefin stream contacts the catalyst and the olefin is reacted with itself or other olefins to form a mixture of dimers, trimers and tetramers polymer. This product passes via line 13 into fractionator 17 where by simple distillation the product is split to recover the oligomer as a bottoms fraction which is removed through line 14 and the unreacted portions removed as an overhead, through line 15, hence to further treatment for separation if desired.

The heat exchange fluid is in indirect contact with the fixed catalyst bed. FIG. 2 shows a conventional and preferred means of obtaining this contact. Reactor 20 is a multitube reactor comprising a shell 30 having mounted therein tubes 22, usually of ⅛ to 2 inches outside diameter. The reactor is shown horizontally, however it could be vertical or inclined. The tubes 22 are mounted through plates 25 and 26 and attached at each end to header plates 23 and 24 which are to prevent fluid communication between the coolant area A, which is adjacent to the tubes, and the feed entry area B and product exit area C. The tubes 22 are in liquid communication with areas B and C. A feed entry pipe 21 is located in the B area and a product exit pipe 27 is located in the C area. Heat exchange medium is provided into the A area via pipe 28 and an exit is provided via pipe 29.

The tubes 22 are packed with the cation exchange resin in granular form 31 and means such as screens (not shown) are fitted to each tube to retain the catalyst therein. FIG. 3 shows an arrangement of tubes 22 in header plate 23.

The reaction is exothermic and the heat exchange medium, e.g., water provides the means for controlling the reaction.

The following examples are presented to illustrate the invention and are not intended to limit its scope. The olefin product analyses were obtained by gas chromatography of the hydrogenated olefins.

EXAMPLE 1

300 ml of Amberlyst 15 (a sulfonated copolymer of styrene and divinyl benzene having a porosity of 32% and surface area of 45 square meters per gram (a product of Rohm and Haas Co.) was placed in a 1-inch O.D. stainless steel reactor tube.

The reactor tube was housed inside a 2½ inch O.D. coaxial tube through which heated water or oil was continually recirculated to maintain the desired reaction temperature. Temperature measurements were made with a calibrated thermocouple inserted into a ⅛ inch O.D. stainless steel tube coaxial to the reactor tube. A feed of n-butenes was passed downflow over the catalyst at reaction conditions of 2–4 LHSV, 100° C. and a pressure of 200 psig. The catalyst was dried prior to use by washing with acetone and drying in a Pyrex dish in an oven at 90° C. for 4–5 hours.

The feed to the reactor contained 20 mole % butane, and typically 47 mole % trans-butene-2, 27 mole % cis butene-2 and 6 mole % butene-1. The oligomerized products from several runs were combined and distilled. The product dimer distilled at 111°–119° C. About 80 mole % of the oligomer product was dimer and gas chromatographic analysis showed 92 mole % of the dimer was dimethylhexenes as follows:

| 3,4 | Dimethylhexenes | 71 mole % |
| --- | --- | --- |
| 2,2 | Dimethylhexenes | 1 mole % |
| 2,4 | Dimethylhexenes | 8 mole % |
| 3,3 | Dimethylhexenes | 3 mole % |
| 2,3 | Dimethylhexenes | 9 mole % |

The analysis also showed the presence of 4 mole % methylheptenes and 1% trimethyl pentenes.

EXAMPLE 2

In the following example, the reactor consisted of a preheat section of coiled ⅛" OD stainless steel tubing connected to ¼" OD stainless steel tubing packed with 25 cc of dry resin as described. Both sections were immersed in a water bath of controlled temperature which is the temperature reported. A back-pressure regulator located downstream of the catalyst bed was used to maintain the desired pressure in the reactor system. Product effluent was collected in a stainless steel, high pressure vessel, downstream of the pressure regulator. After a sufficient volume of effluent had been collected for analysis, the contents of the SS vessel were transferred to a tared and evacuated Pyrex bottle fitted with a rubber septum mounted in a perforated metal cap. A 20-gauge needle attached to the SS vessel was inserted through the rubber septum of the bottle and the reaction products were collected for weighing. The contents of the Pyrex bottle were then evaporated at room temperature and later at 90° F. via a transfer line into a second evacuated bottle immersed in a mixture of acetone and solid $CO_2$. Separation of the lower boiling, unreacted $C_4$ hydrocarbons from the higher boiling oligomerized products was thus effected, and the weight percent of oligomers calculated. The composition of each of the two hydrocarbon fractions was determined chromatographically.

The feed to the reactor was 4.34 mole % normal butane, 0.67 mole % butene-1, 57.63 mole % trans butene-2 and 37.34 mole % cis butene-2. The catalyst was Amberyst 15 (a Rohm and Haas product) which had been washed with acetone and dried prior to use. The reaction temperature (determined by the temperature of the water bath) was between 90° and 100° C. at 400 psig, and LHSV=2.3–4.6. At 77 hours on stream 73.4 wt.% oligomers were produced. The product was analysed by hydrogenation gas chromatography and showed: 3,4-dimethyl hexene=68 mole %, 3-methyl heptene=6 mole %, 2,3,4-trimethyl pentene=1 mole %, 2,3-dimethyl hexene=9 mole %, 3,3-dimethyl hexene=3 mole %, 2,4-dimethyl hexene=11 mole %, 2,5-plus 2,2-dimethyl hexene=1 mole %.

EXAMPLE 3

The reactor was the same as Example 2. The catalyst was twenty-five grams of Amberlyst XN-1010 (a sulfonated copolymer of styrene and divinyl benzene having a porosity of 47% and surface area of 570 square meters per gram) product of Rohm & Haas Co. The reactor feed was a $C_4$ stream having the following analysis:

| Neopentene | 0.01 | mole % |
|---|---|---|
| Normal butane | 21.86 | mole % |
| Butene-1 | 0.28 | mole % |
| Trans butene-2 | 47.84 | mole % |
| Cis butene-2 | 29.98 | mole % |

The conditions of reaction were: temperature 100° C., pressure 300 psig; LHSV=2.5. At 18 hours on stream the product was 49.1 wt.% oligomer. Near the end of the run, at 25% conversion of butenes, the dimer had the following gas-chromatographic analysis: 3,4-dimethyl hexene=88 mole %, 3-methyl heptene=6 mole %, 2,3 dimethyl hexene plus 2,3,4-trimethyl pentene=1 mole %, 3,3-dimethyl hexene=1 mole %, 2,4-dimethyl hexene=4 mole %.

EXAMPLE 4

The reactor was a jacketed ½" O.D. 316 SS reactor tube (with coaxial ⅛" O.D. 306 SS thermowell) containing 50 cc of catalyst. The reactor was heated with recirculated oil from a constant temperature bath and entered at the bottom of the jacket and exited at the top. Liquid hydrocarbons were fed to the top of the reactor and exited at the bottom. The reactor contained 50 cc of Amberlite 252H catalyst (a sulfonated styrene divinyl benzene copolymer) product of Rohm & Haas Co. The conditions were: temperature 100° C., pressure 225 psig; LHSV 2.5. The feed composition was: 21.9 mole % n-butane, 0.3 mole % butene-1, 47.8 mole % trans butene-2, 30.0 mole % cis butene-2. After 420 hours on stream, the reactor effluent contained 33.6 weight % oligomer of which 85% was dimer. At 700 hours on stream, the dimer had the following analysis: 3,4-dimethyl hexene=73 mole %, 3-methyl heptene=11 mole %, 2,3-dimethyl hexene plus 2,3,4-trimethyl pentene=6 mole %, 3,3-dimethyl hexene=3 mole %, 2,4-dimethyl hexene=7 mole %.

EXAMPLE 5

The feedstock used was butene-1 (99.9%) in the reactor of Example 2 with conditions similar to those in Example 2 except that the temperature was 80° C. The product dimer contained 2,4-dimethyl hexene=10 mole %, 2,3-dimethyl hexene, plus 2,3,4-trimethyl pentene=6 mole %, 3,4-dimethyl hexene=72 mole %, 3-methyl heptene=6 mole %, 3,3-dimethyl hexene=4 mole %, and 2,2-plus 2,5-dimethyl hexene=1 mole % at 17.3 mole % conversion of the n-butene 1.

EXAMPLE 6

Using the reactor of Example 4 with a 80 mole % butene-2, 20 mole % n-butane feed at an inlet temperature of 99° C. and a measured exotherm to 145° C. (Δ46° C.), a conversion of 77.7 mole % produced an oligomer of the following analysis: 3,4-dimethyl hexene=mole %, 3-methyl heptene=6 mole %, 2,3-dimethyl hexene=6 mole %, 2,3,4-tri-methyl pentene=1 mole %, 3,3-dimethyl hexene=2 mole %, 2,4-dimethyl hexene=12 mole %, 2,2-dimethyl hexene=1 mole %, $C_{12}$ plus $C_{16}$=33 mole %.

EXAMPLE 7

This example demonstrates the operation of the process at low temperature and low LHSV. The reactor and catalyst of Example 4 was employed. The feed to the reactor was 15.1 mole % n-butane, 1.2 mole % butene-1. 48.9 mole % trans butene-2 and 33.1 mole % cis butene-2. The pressure was 250 psig and LHSV was 0.5. Two temperatures were used. At 40° C., 3.0 wt.% oligiomer was produced at 115 hours on stream and at 44° C., 7.4 wt.% oligomer was produced at 91 hours on stream.

The dimer product of n-butenes according to the present process are novel and different from those of prior art processes. Surprisingly, the product is relatively uniform as to isomer distribution over the range of process conditions. The very high dimethylhexene fraction of the dimer is especially unique.

It has been found that the dimer product of n-butene as well as the entire oligomer product have very high research octane and motor octane numbers (typically 95 andand 82, respectively).

A particularly valuable use for the $C_8$ dimer or oligomer fraction is a feed for hydrocarbonylation (oxonation reaction) to produce long chain alcohols. The prior art dimer product has been employed for this purpose and the resultant alcohols are used as plasticizers, surface active agents and pesticides. Because of the presence of only a few octenes in large concentrations (>10%), of desirable structure, the hydrocarbonylated $C_8$ dimer of the present invention exhibits unexpected improved qualities as an oxonation feedstock to produce plasticizers for polymers. The higher $C_4$ oligomers and other olefin oligomers of about $C_{12}$ are useful as gasoline blending stocks; and higher carbon chain lengths produce viscous liquids useful as oil viscosifiers or synthetic lubricants and plasticizers.

I claim:
1. A process for producing dimers of normal butenes comprising
   (a) contacting a feed in liquid phase containing at least 70 mole % normal butenes having less than 1 mole % isobutene with a fixed bed cation exchange resin having a granular size of about 0.25 to 2 mm in indirect contact with a fluid heat exchange medium at a temperature in the range of 80° C. to 130° C. at a liquid hourly space velocity of 2 to 5,
   (b) reacting the n-butenes to form oligomers thereof to form a product stream containing a predominant amount of dimer of normal butenes and unreacted feed components, and
   (c) removing said product stream from said reactor.
2. The process according to claim 1 wherein said feed to said catalyst is free of entrained, second phase water.
3. The process according to claim 1 wherein said feed is substantially hydrocarbons having four carbon atoms.
4. The process according to claim 1 wherein the pressure is in the range of 50 to 3500 psig.
5. The process according to claim 1 wherein said product stream is fractionated to separate said oligomers and unreacted feed components.
6. The process according to claim 5 wherein said oligomer is recovered as a bottoms product and unreacted feed components recovered as an overhead in a distillation.
7. The process according to claim 6 wherein the normal olefins are normal butenes.

* * * * *

UNITED STATES PATENT OFFICE
CERTIFICATE OF CORRECTION

PATENT NO. : 4,463,211

DATED : July 31, 1984

INVENTOR(S) : Harold E. Manning

It is certified that error appears in the above-identified patent and that said Letters Patent are hereby corrected as shown below:

Col. 3, line 26 reads " a predominately" but should read --- predominately ---

Col 7, line 66 reads "3,4-dimethyl hexene = mole" but should read --- 3,4-dimethyl hexene = 32 mole ---

Col. 8, line 24 reads "andand" but should read --- and ---

Signed and Sealed this

Twenty-third Day of September 1986

[SEAL]

Attest:

DONALD J. QUIGG

Attesting Officer     Commissioner of Patents and Trademarks